United States Patent [19]
Crow et al.

[11] Patent Number: 6,111,153
[45] Date of Patent: Aug. 29, 2000

[54] PROCESS FOR MANUFACTURING METHYL CHLORIDE

[75] Inventors: Robert Dennis Crow, Penarth; Neil Philip Roberts, Gwent, both of United Kingdom

[73] Assignees: Dow Corning Corporation, Midland, Mich.; Dow Corning Limited, South Glamorgan, United Kingdom

[21] Appl. No.: 09/323,411

[22] Filed: Jun. 1, 1999

[51] Int. Cl.⁷ ..................................................... C07C 17/00
[52] U.S. Cl. ............................................................ 570/258
[58] Field of Search ............................................. 570/258

[56] References Cited

U.S. PATENT DOCUMENTS 4,922,043  5/1990  Petrosky ................................. 570/258
4,935,564  6/1990  Bunce et al. ............................ 570/258

*Primary Examiner*—Alan Siegel
*Attorney, Agent, or Firm*—Melvin D. Fletcher

[57] ABSTRACT

A process for manufacturing methyl chloride. The process consists essentially of contacting hydrogen chloride with at least a stoichiometric amount of methanol split into at least two portions with a first portion comprising about 60 to 95 percent of the methanol added to the process in the presence of a first liquid medium at a temperature in the range of about 115° C. to 170° C. to form a gaseous mixture containing methyl chloride, and contacting the gaseous mixture with a second methanol portion and adding to a second liquid medium at a temperature in the range of about 100° C. to 160° C., and recovering the methyl chloride.

19 Claims, 1 Drawing Sheet

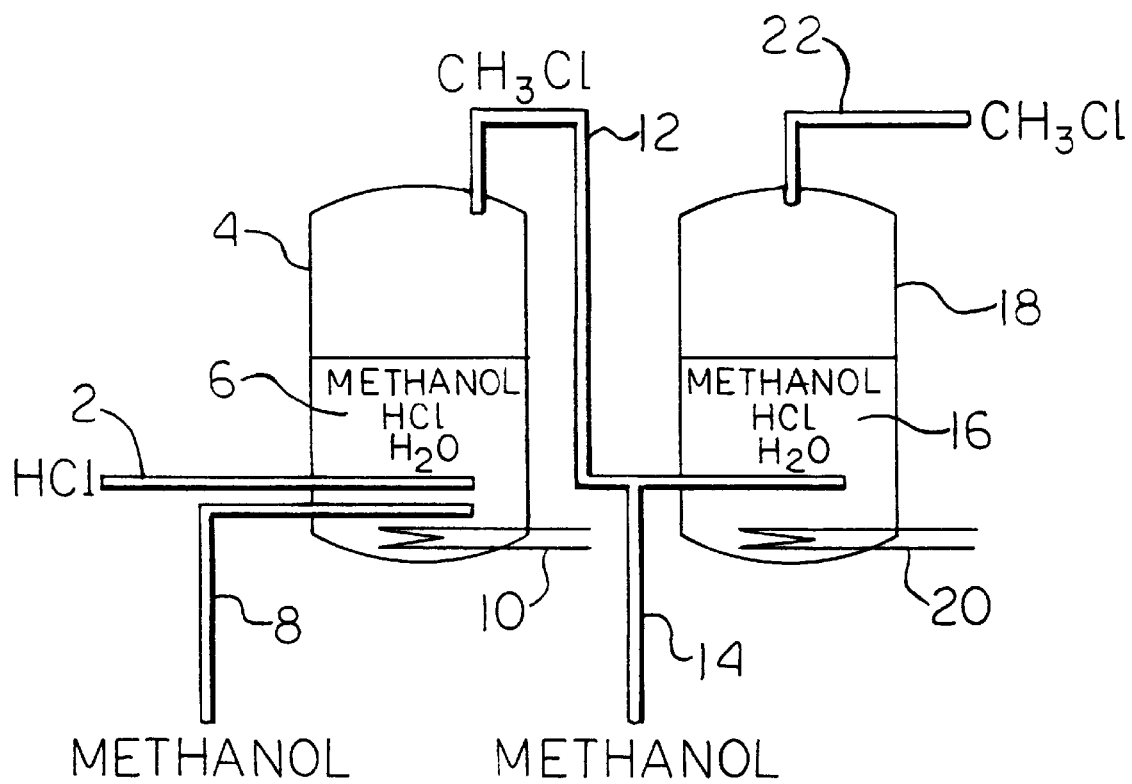

PROCESS FOR MANUFACTURING METHYL CHLORIDE

BACKGROUND OF INVENTION

The present invention is a process for manufacturing methyl chloride. The process consists essentially of contacting hydrogen chloride with at least a stoichiometric amount of methanol split into at least two portions with a first portion comprising about 60 to 95 percent of the methanol added to the process in the presence of a first liquid medium at a temperature in the range of about 115° C. to 170° C. to form a gaseous mixture containing methyl chloride, and contacting the gaseous mixture with a second methanol portion and adding to a second liquid medium at a temperature in the range of about 100° C. to 160° C., and separating and recovering the methyl chloride.

The preparation of methyl chloride by contacting hydrogen chloride with methanol has been conducted using catalyzed processes in gas and liquid phases. Moreover, many processes are carried out using an excess of hydrogen chloride relative to methanol resulting in unreacted hydrogen chloride and dimethyl ether as a by-product. Due to the corrosive nature of hydrogen chloride and the ecological concerns of discharging hydrogen chloride into the environment, unreacted hydrogen chloride recovery is a time and capital intensive process. Furthermore, it is difficult to recover unreacted hydrogen chloride because it forms an azeotropic mixture with water which makes separation by distillation extremely difficult. In a typical process for removing dimethyl ether from methyl chloride, the methyl chloride is contacted with concentrated sulfuric acid producing a dilute sulfuric acid stream contaminated with methyl sulfates. Formation of the dilute sulfuric acid stream is wasteful in terms of greater raw material costs, and disposal of unwanted sulfuric acid containing dimethyl ether presents ecological concerns as well.

Bunce et al., U.S. Pat. No. 4,935,564, describe a process for preparing an alkyl halide from contacting and reacting a hydrogen halide with a stoichiometric excess of alcohol in a plug-flow reactor in which flow of a mixture comprising unreacted alcohol, unreacted hydrogen halide, the alkyl halide, and water is co-current.

Petrosky, U.S. Pat. No. 4,922,043, describes a process for making methyl chloride by catalytic hydrochlorination of methanol in the liquid phase by feeding hydrogen chloride into a first reactor while splitting methanol feed between or among the reactors. The process uses a stoichiometric excess of hydrogen chloride to methanol and requires a hydrogen chloride recovery system.

The present inventors have discovered that by feeding all the hydrogen chloride into a first reactor and splitting the methanol feed between multiple reactors, reduced levels of dimethyl ether by-product were demonstrated by proportionately increasing methanol fed to a second reactor and proportionately decreasing methanol to the first reactor. Furthermore, feeding a stoichiometric excess of methanol relative to hydrogen chloride results in a higher hydrogen chloride percentage conversion to methyl chloride. Increasing the hydrogen chloride conversion percentage to methyl chloride eliminates processing steps for hydrogen chloride recovery and recycle. Decreasing dimethyl ether formation reduces sulfuric acid use and the ecological concerns and disposal cost associated with sulfuric acid use.

SUMMARY OF INVENTION

The present invention is a process for manufacturing methyl chloride. The process consists essentially of contacting hydrogen chloride with at least a stoichiometric amount of methanol split into at least two portions with a first portion comprising about 60 to 95 percent of the methanol added to the process in the presence of a first liquid medium at a temperature in the range of about 115° C. to 170° C. to form a gaseous mixture containing methyl chloride, and contacting the gaseous mixture with a second methanol portion and adding to a second liquid medium at a temperature in the range of about 100° C. to 160° C., and recovering the methyl chloride.

DESCRIPTION OF THE DRAWING

FIG. 1 is a representative schematic flow diagram of one embodiment for the present process for manufacturing methyl chloride. This representation is presented to be illustrative and is not to be construed as limiting the present process.

DETAILED DESCRIPTION OF THE INVENTION

In FIG. 1, anhydrous hydrogen chloride gas 2 (HCl) is fed to first reactor 4 containing first liquid medium 6. The HCl 2 is contacted with first methanol portion 8 in the presence of first liquid medium 6. First reactor 4 is heated by heating coil 10 to form gaseous mixture 12 containing methyl chloride. Gaseous mixture 12 is withdrawn from first reactor 4 in the vapor phase and is contacted with second methanol portion 14 and fed to second liquid medium 16 contained in second reactor 18 connected in series with first reactor 4. Second reactor 18 is heated by heating coil 20. The gaseous mixture containing mostly methyl chloride 22 is withdrawn from second reactor 18 and then the methyl chloride is recovered and subsequently purified by conventional methods.

The present invention is a process for manufacturing methyl chloride. The process consists essentially of contacting hydrogen chloride with at least a stoichiometric amount of methanol split into at least two portions with a first portion comprising about 60 to 95 percent of the methanol added to the process in the presence of a first liquid medium at a temperature in the range of about 115° C. to 170° C. to form a gaseous mixture containing methyl chloride, and contacting the gaseous mixture with a second methanol portion and adding to a second liquid medium at a temperature in the range of about 100° C. to 160° C., and recovering the methyl chloride.

The present process may be run in any pressurizable reactor suitable for contact with hydrogen chloride. The process may be run as a batch process or preferably as a continuous process. The process may be run, for example, in a continuous stirred-tank reactor, a bubble-column reactor, or a plug-flow reactor.

The hydrogen chloride can be fed to the process as an anhydrous gas, and preferably all of the hydrogen chloride is fed to the process at once. In an alternative embodiment, aqueous hydrochloric acid comprising hydrogen chloride and water can be fed to the process. The methanol utilized in the process may be liquid, but is preferably partially vaporized by conventional means and fed to the process in a mostly gaseous phase. Preferably the methanol is preheated to a temperature above 90° C. before feeding it to the process to help disperse the methanol and control the temperature of the process. Most preferably the methanol is preheated to a temperature in the range of about 90° C. to 170° C. before being fed to the process. The amount of methanol fed to the process is split into multiple portions with a first portion comprising greater than 60 percent of the methanol added to the process. Preferably, the amount of methanol is split into two portions with the first portion comprising about 60 to 95 percent of the total amount of methanol added to the process. Most preferred the amount of methanol is split into two portions with the first portion comprising about 70 to 90 percent of the total amount of methanol added to the process.

The contacting of the hydrogen chloride with at least a stoichiometric amount of methanol is conducted in the presence of a first liquid medium comprising methanol, hydrogen chloride, and water which is preferably maintained at a constant concentration and level within the first reactor. It is preferable to effect the contact of the hydrogen chloride and methanol by adding the hydrogen chloride and first methanol portion in the first liquid medium at or near the bottom of the first reactor to increase dispersion into the first liquid medium. Typically the first liquid medium concentration is about 5 to 30 weight percent hydrogen chloride, one to 10 weight percent methanol and the remainder water. Preferably the first liquid medium concentration is about 10 to 20 weight percent hydrogen chloride and about 3 to 7 weight percent methanol.

The contacting of the hydrogen chloride with the first methanol portion in the presence of the first liquid medium is conducted within a temperature range of about 115° C. to 170° C. Preferably the temperature is within the range of about 120° C. to 135° C. The temperature and pressure are maintained to vaporize the gaseous mixture containing methyl chloride from the first liquid medium and to maintain the first liquid medium at a constant level. Preferably the pressure is in the range of about 240 to 900 kPaG. Most preferably the pressure is in range of about 240 to 500 kPaG.

In the formation of the gaseous mixture containing methyl chloride, about 80 to 90 percent of the hydrogen chloride added to the process is converted to methyl chloride. The gaseous mixture containing methyl chloride typically may contain a portion of unreacted hydrogen chloride, methanol, by-product dimethyl ether and water.

The gaseous mixture containing methyl chloride is withdrawn from the first reactor as a vapor, and contacted with the second methanol portion and added to a second liquid medium comprising methanol, hydrogen chloride, and water maintained in a second reactor connected to the first reactor. The second methanol portion reacts with the unreacted hydrogen chloride contained in the gaseous mixture and the unreacted hydrogen chloride is converted to additional methyl chloride. Water formed in the second medium is vaporized and withdrawn from the second reactor. In an alternative embodiment of the present process the gaseous mixture containing methyl chloride is contacted with the second methanol portion in the presence of a second liquid medium comprising methanol, hydrogen chloride, and water. The second methanol portion may be in a gaseous phase, and partially vaporized, but is preferably a liquid. Preferably the first and second reactors are connected in series. It is desirable that the gaseous mixture and the second methanol portion be dispersed through the second liquid medium at or near the bottom of the second reactor.

The contacting of the gaseous mixture containing methyl chloride with the second methanol portion is conducted at a temperature within the range of about 100° C. to 160° C. Preferably the temperature is within the range of about 110° C. to 125° C. The temperature and pressure are maintained to continuously vaporize the gaseous mixture containing methyl chloride and portions of unreacted hydrogen chloride, methanol, by-product dimethyl ether, and water from the second liquid medium, thereby providing a continuous process.

In the present process the gaseous mixture containing methyl chloride has at least a stoichiometric amount of methanol to hydrogen chloride. Preferably, there is a stoichiometric excess in the range of 1.2 to 1.6 moles methanol per mole hydrogen chloride. Most preferably, there is an excess of 1.3 to 1.4 moles methanol per mole hydrogen chloride. Furthermore, it has been found that feeding a stoichiometric excess of methanol relative to hydrogen chloride significantly improves hydrogen chloride conversion to methyl chloride. After the second reactor, greater than 98 percent of the hydrogen chloride added to the process is converted to methyl chloride.

The space-time yield for the production of the methyl chloride produced by the present process is within the range of about 100 to 300 kg/hr.m$^3$. Preferably, the space-time yield is within the range of about 150 to 300 kg/hr.m$^3$, however the space-time yield could be in excess of 300 kg/hr.m$^3$. The "space-time yield" is defined as the productivity per unit volume of the reactors per unit time.

The gaseous mixture containing methyl chloride is withdrawn from the second reactor and may contain small amounts of unreacted hydrogen chloride, methanol, water and by-product dimethyl ether. The methyl chloride may be separated and recovered from the gaseous mixture by, for instance, condensing out the unreacted methanol, water, and hydrogen chloride and recovering the methyl chloride by distillation. The unreacted methanol can be separated and recovered from the liquid phase by such known techniques as distillation, and the recovered methanol recycled to the reactors. The water resulting from the separation along with a small amount of hydrogen chloride can be discarded. The methyl chloride can be purified by contacting with sulfuric acid and liquefied for storage by compression and cooling.

Unlike processes known in the art, the contacting of the hydrogen chloride with at least a stoichiometric amount of methanol in a liquid medium to produce methyl chloride is effected in the absence of a catalyst.

The following examples are provided to illustrate the present invention, the examples are not intended to limit the present claims.

EXAMPLE 1

For run 1, anhydrous hydrogen chloride (3000 kg/hr) and 3168 kg/hr of methanol at a temperature of about 110° C. and partially vaporized were fed into a continuous reactor (first reactor) containing a first liquid medium comprising water, hydrogen chloride and methanol. The first reactor temperature was maintained at about 130° C. and the pressure above the first liquid medium at about 280 kPaG. The first reactor contained about 88 percent of the total amount of methanol fed to the process. The gaseous mixture containing methyl chloride exiting as an overhead vapor was contacted with 432 kg/hr second methanol portion and then fed to a second liquid medium maintained in a second reactor connected in series with the first reactor. The second reactor temperature was maintained at about 117° C. and the pressure at 250 kPaG. The mole ratio of methanol fed to the process was about 1.36 moles methanol per mole hydrogen chloride. The gaseous mixture exiting the second reactor was analyzed by gas chromatography (GC) to determine the level of dimethyl ether by-product produced. A condensed portion of the gaseous mixture was analyzed by conventional titration with a base to determine hydrogen chloride content. Table 1 contains a summary of the run results, the anhydrous hydrogen chloride and methanol feed rates in kg/hr, which are designated as "HCl" and "MeOH", respectively; the MeOH to HCl mole ratio designated as "Ratio"; the percent MeOH fed to the first reactor designated as "MeOH Split"; the amount of dimethyl ether formed in kg of dimethyl ether per 1000 kg of MeCl designated as "DME"; and the percent hydrogen chloride converted to methyl chloride designated as "HCl %".

TABLE 1

| Run | HCl | MeOH | MeOH Split | Ratio | HCl % | DME |
|---|---|---|---|---|---|---|
| 1 | 3000 | 3600 | 88 | 1.36 | 99.5 | 11 |
| 2 | 3500 | 4200 | 86 | 1.36 | 99.3 | 9 |
| 3 | 3400 | 4080 | 83 | 1.36 | 99.3 | 8.3 |
| 4 | 3400 | 4080 | 82 | 1.36 | 99.3 | 8.0 |
| 5 | 3400 | 4080 | 80 | 1.36 | 99.2 | 7.8 |
| 6 | 3400 | 4080 | 78 | 1.36 | 99.1 | 7.5 |

EXAMPLE 2

Evaluation to manufacture methyl chloride by feeding 78 to 86 percent of the methanol to the first reactor and 14 to 22 percent of the methanol to the second reactor. The procedure of Example 1 was repeated while varying the hydrogen chloride and methanol fed to the process and the amount of methanol fed to the first and second reactors as indicated in Table 1. The results from runs 2 to 6 are reported in Table 1.

We claim:

1. A process for manufacturing methyl chloride consisting essentially of:
   (A) contacting hydrogen chloride with at least a stoichiometric amount of methanol split into at least two portions with a first portion comprising about 60 to 95 percent of the methanol added to the process in the presence of a first liquid medium at a temperature in the range of about 115° C. to 170° C. to form a gaseous mixture containing methyl chloride, and
   (B) contacting the gaseous mixture with a second methanol portion and adding to a second liquid medium at a temperature in the range of about 100° C. to 160° C., and
   (C) recovering the methyl chloride.

2. A process according to claim 1, where the amount of methanol is split into multiple portions with the first portion comprising about 78 to 90 percent of the methanol added to the process.

3. A process according to claim 1, where the hydrogen chloride is contacted with at least a stoichiometric amount of methanol in the presence of the first liquid medium at a temperature in the range of about 120° C. to 135° C.

4. A process according to claim 1, where the gaseous mixture is contacted with the second methanol portion and added to the second liquid medium at a temperature in the range of about 110° C. to 125° C.

5. A process according to claim 1, where the first methanol portion is partially vaporized and fed to the process.

6. A process according to claim 1, where the first methanol portion is preheated to a temperature in the range of about 90° C. to 170° C. before being fed to the process.

7. A process according to claim 1, where the first and second liquid medium each comprises methanol, hydrogen chloride, and water.

8. A process according to claim 1, where the concentration of the first liquid medium is about 5 to 30 weight percent hydrogen chloride, one to 10 weight percent methanol and the remainder water.

9. A process according to claim 1, where the concentration of the first liquid medium is about 10 to 20 weight percent hydrogen chloride, and about 3 to 7 weight percent methanol and the remainder water.

10. A process according to claim 1, where the contacting is conducted at a pressure in the range of about 240 to 900 kPaG.

11. A process according to claim 1, where the contacting is conducted at a pressure in the range of about 240 to 500 kPaG.

12. A process according to claim 1, where the process is conducted as a continuous process.

13. A process according to claim 1, where there is a stoichiometric excess in the range of 1.2 to 1.6 moles methanol per mole hydrogen chloride.

14. A process according to claim 1, where there is a stoichiometric excess in the range of 1.3 to 1.4 moles methanol per mole hydrogen chloride.

15. A process according to claim 1, where the process has a space-time yield within a range of about 100 to 300 kg/hr.m³.

16. A process according to claim 1, where the process has a space-time yield within a range of about 150 to 300 kg/hr.m³.

17. A process according to claim 1, further comprising contacting the recovered methyl chloride with sulfuric acid.

18. A process according to claim 1, where the second methanol portion is partially vaporized.

19. A process for manufacturing methyl chloride consisting essentially of:
   (A) contacting aqueous hydrochloric acid with at least a stoichiometric amount of methanol split into at least two portions with a first portion comprising about 60 to 95 percent of the methanol added to the process in the presence of a first liquid medium at a temperature in the range of about 115° C. to 170° C. to form a gaseous mixture containing methyl chloride, and
   (B) contacting the gaseous mixture with a second methanol portion and adding to a second liquid medium at a temperature in the range of about 100° C. to 160° C., and
   (C) recovering the methyl chloride.

* * * * *